(12) United States Patent
Downer et al.

(10) Patent No.: US 6,411,388 B1
(45) Date of Patent: Jun. 25, 2002

(54) SYSTEM AND METHOD FOR FREQUENCY DOMAIN INTERFEROMETRIC SECOND HARMONIC SPECTROSCOPY

(75) Inventors: Michael W. Downer, Austin, TX (US); Philip T. Wilson, Olney, MD (US)

(73) Assignee: Board of Regents The University of Texas System, Austin, TX (US)

(*) Notice: Subject to any disclaimer, the term of this patent is extended or adjusted under 35 U.S.C. 154(b) by 8 days.

(21) Appl. No.: 09/722,998

(22) Filed: Nov. 27, 2000

Related U.S. Application Data
(60) Provisional application No. 60/167,997, filed on Nov. 30, 1999.

(51) Int. Cl.$^7$ .................................................. G01J 3/45
(52) U.S. Cl. ........................ 356/451; 356/450; 356/453
(58) Field of Search ............................... 356/451, 453, 356/450

(56) References Cited

U.S. PATENT DOCUMENTS

| | | | | |
|---|---|---|---|---|
| 4,184,737 A | * | 1/1980 | Hirschberg | 350/13 |
| 4,426,155 A | | 1/1984 | Monchalin | 356/346 |
| 4,684,255 A | | 8/1987 | Ford | 356/346 |
| 4,906,095 A | | 3/1990 | Johnston | 356/349 |
| 5,557,409 A | | 9/1996 | Downer et al. | 356/371 |
| 5,623,338 A | | 4/1997 | Wickramasinghe et al. | 356/357 |
| 5,623,339 A | | 4/1997 | Wickramasinghe et al. | 356/357 |
| 5,781,297 A | | 7/1998 | Castore | 356/349 |
| 5,872,629 A | | 2/1999 | Colvard | 356/349 |
| 6,219,142 B1 | * | 4/2001 | Kane | 356/450 |

* cited by examiner

*Primary Examiner*—Samuel A. Turner
*Assistant Examiner*—Phil Natividad
(74) *Attorney, Agent, or Firm*—Sanford E. Warren, Jr.; Edwin S. Flores; Gardere Wynne Sewell LLP

(57) ABSTRACT

A method of spectroscopically analyzing amplitude and phase information of a particular sample (510) is disclosed, comprising providing a femtosecond laser source (502) positioned in an angularly distal relationship to the sample, generating from the laser source a primary light pulse (504) of substantial peak intensity and spectral bandwidth directed at the sample, and providing a reference medium (512) interposed between the light source and the sample, fixed in position with respect to the sample. A portion of the primary light pulse is directed through the reference medium generating a reference second harmonic signal (514) directed at the sample, which propagates collinearly with the primary light pulse towards the sample. A spectrometer (520) is provided, positioned in an angularly distal relationship to the sample and opposing the laser source, to receive second harmonic reflections of the primary pulse and reference signal (516 and 514, respectively) from said sample. The second harmonic reflections received are then analyzed.

20 Claims, 8 Drawing Sheets

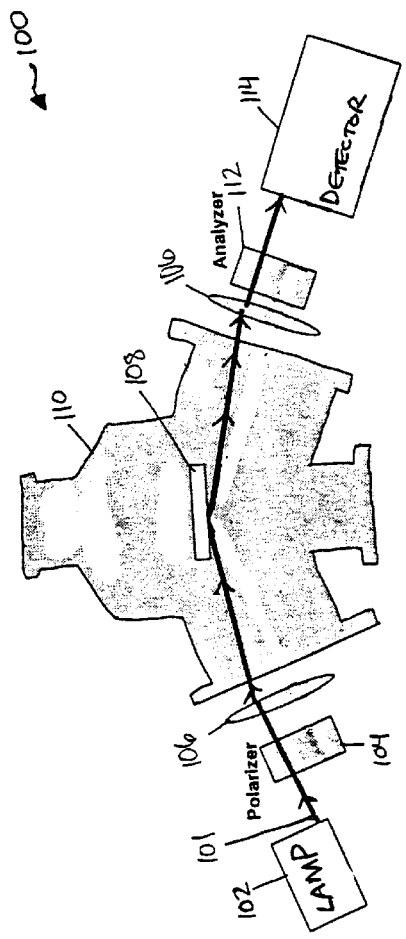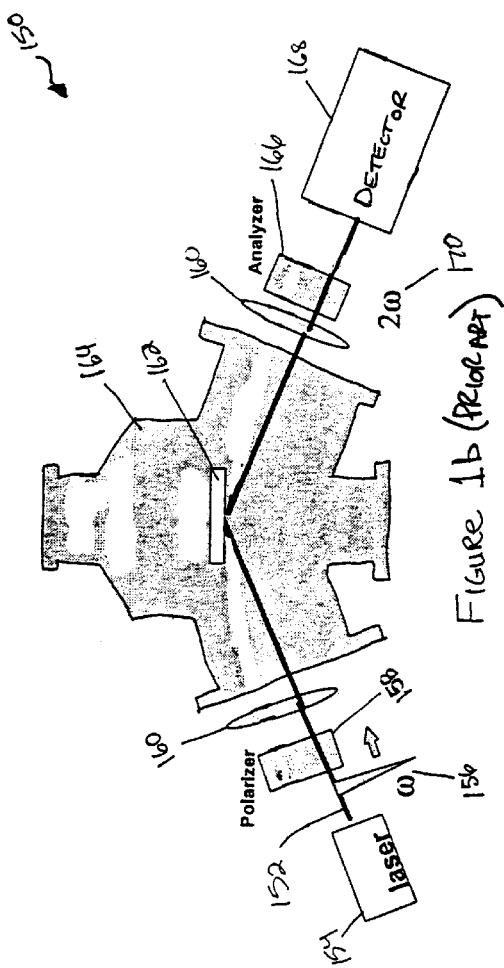

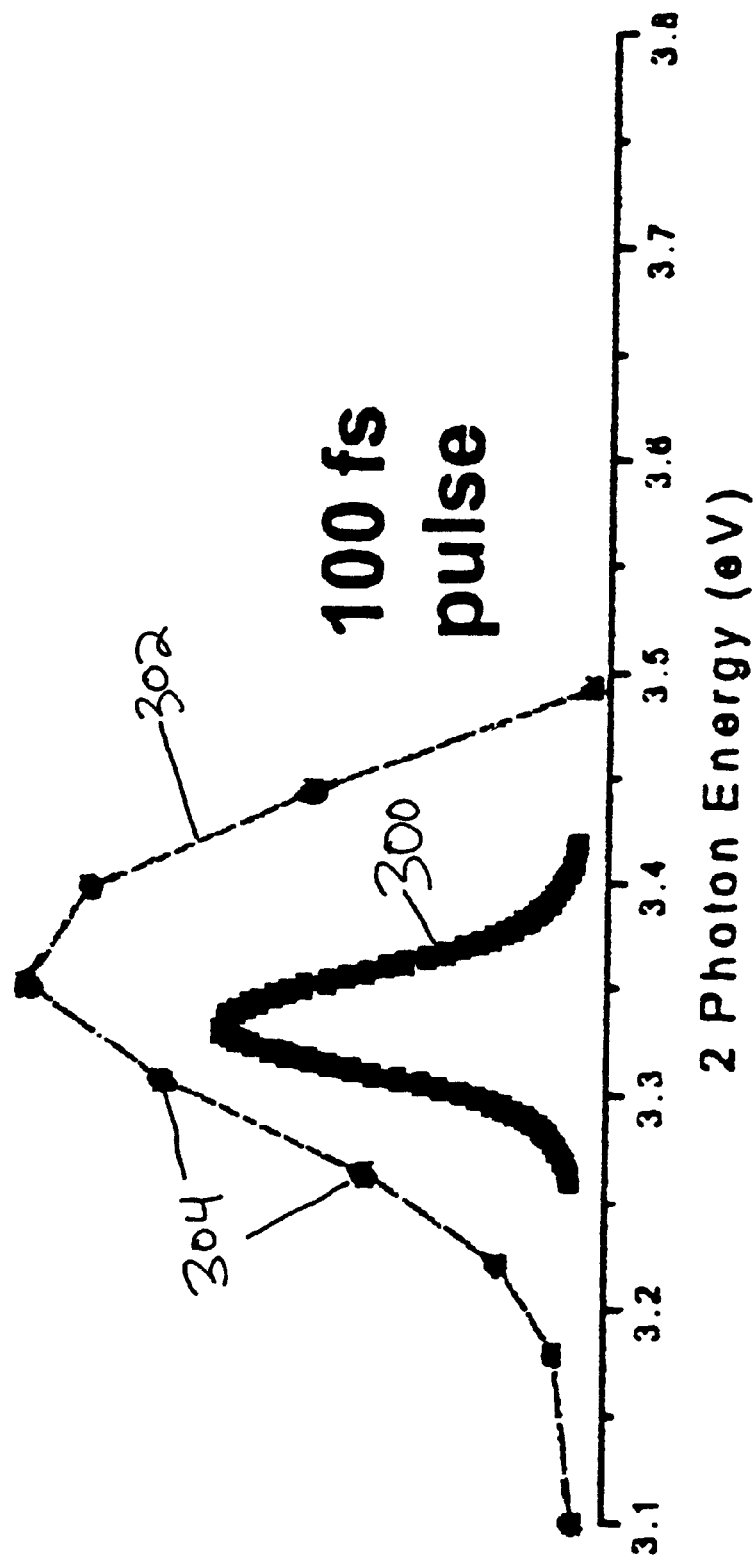

SYSTEM AND METHOD FOR FREQUENCY DOMAIN INTERFEROMETRIC SECOND HARMONIC SPECTROSCOPY

We hereby claim benefit under 35 U.S.C. §119(e) of U.S. Provisional Application Ser. No. 60/167,997, filed Nov. 30, 1999.

TECHNICAL FIELD OF THE INVENTION

The present invention relates, in general, to non-linear spectroscopy systems and, in particular, to a system and method for simultaneously measuring the amplitude and phase of second harmonic radiation over a broad spectral range without laser tuning.

BACKGROUND OF THE INVENTION

The continual demand for enhanced integrated circuit performance has resulted in numerous advancements in semiconductor processes. One example of such advancement is a considerable scaling down of semiconductor process feature sizes. While such scaling has improved certain performance aspects, it has also created a number of challenges in areas such as fine feature measurement and characterization during production. Spectroscopy systems and techniques are widely used to provide detail measurement and characterization in such applications.

Spectroscopy systems are commonly used to non-invasively measure the properties or states of a semiconductor surface or sub-surface interface by analyzing light reflected therefrom. A typical objective of spectroscopy is the measurement of phase shift in the light reflected from the material under examination. Spectroscopy systems generally fall within one of two categories: linear spectroscopy or non-linear spectroscopy. Linear spectroscopy systems and non-linear spectroscopy systems typically differ in their ability to detect and characterize phenomena and material properties of particular interest; and are therefore generally employed in different applications.

Linear spectroscopy systems are typically characterized by operation involving a single wavelength of light. Linear systems typically use lamps (e.g. incandescent or arc lamps) as a light source; and typically examine a sheath-like area around the surface of interest. Conventionally, linear systems are employed to measure bulk properties of some material, such as film thickness or a varying chemical composition. For example, in a typical semiconductor processing application, a linear system would measure thickness and composition of a epitaxial growth film.

In comparison, non-linear spectroscopy systems are typically characterized by operation involving varying wavelengths of light. Typically, a high intensity light source, such as a laser, is used. Non-linear systems possess unique diagnostic capabilities due, in part, to a high surface specificity and sensitivity. This means that the reflection point from the item under examination is confined to one or two atomic layers in the immediate area of a surface or sub-surface interface.

This comparison is illustrated with reference now to FIGS. 1a and 1b. FIG. 1a provides a representative illustration of a linear spectroscopy system, specifically a spectroscopic ellipsometer 100. In ellipsometer 100, light 101 emitted from source 102 (typically an incoherent white light source such as a Xenon arc lamp) is filtered through a polarizing element 104, and directed by focusing element 106 (typically a lens) at a target sample 108 (e.g. SiGe) within processing unit 110 (e.g. a Chemical Vapor Deposition chamber). Light 101 is reflected from sample 108 through a second element 106, passing through analyzer element 110 (e.g. a polarization analyzer) to detector 114; where data such as the amplitude of the reflected light is evaluated.

FIG. 1b provides a representative illustration of a second harmonic (SH), non-linear spectroscopy system 150. In system 150, light 152 emitted from source 154 (typically a laser), with frequency 156 of ω is filtered through polarizing element 158, and directed by focusing element 160 (typically a lens) at a target sample 162 (e.g. SiGe) within processing unit 164 (e.g. a Chemical Vapor Deposition chamber). Light 152 is non-linearly reflected from sample 162 through a second element 160, passing through analyzer element 166 (e.g. a polarization analyzer) to detector 168; detecting light at twice the incident frequency (2ω) 170 created by the non-linear reflection. Detector 168 evaluates data such as the amplitude of the reflected light.

Thus, the spectra of the reflected light is used to measure material properties. System 100 detects light at the same optical frequency as the incident light reflected from the sample. System 150 detects light at twice the incident frequency created by non-linear reflection. System 100 measurement therefore characterizes bulk properties of a sample, such as thickness and average composition of an epitaxial film; while system 150 measurement characterizes properties of the interface or surface of the film, such as surface composition, interface dc electric fields, and atomic and molecular adsorption, which can used to evaluate growth chemistry and rates. This information is of particular interest in semiconductor processing.

For semiconductor processing applications, spectroscopy system users are typically interested in characterizing the interface between a growing film and its substrate; for purposes such as detecting the presence of contamination or improper bonding, or measuring material strain. As previously presented, linear reflected light is insensitive to such phenomenon; compelling users to either employ non-linear systems or other alternative methods of measurement and characterization.

This presents a dilemma, however, because spectroscopy users need systems that are compact, inexpensive, simple to use. Conventional linear systems often possess these characteristics, making them a viable choice for use in high volume commercial production. Previously, non-linear spectroscopy systems have not been commercially viable, and thus limited to research and academic applications, because nobody has been able to produce them in a compact, simple to use, or inexpensive manner. Therefore, conventional commercial spectroscopy systems are typically linear in nature. For example, linear systems such as spectroscopic ellipsometers are widely used in the semiconductor industry.

Further, conventional non-linear systems are difficult to use in certain spectroscopic modes; particularly in sampling different wavelengths of second-harmonic (SH) reflected light. To examine varying wavelengths of SH reflected light, conventional systems require a manual tuning process. This results in a serial mode of data acquisition (i.e. sampling one wavelength at a time); which decreases the speed and efficiency of such systems, and increases their complexity of use. Additionally, conventional non-linear systems typically are limited in phase shift measurement; again requiring serial mode data acquisition and complex, time-consuming movement of system apparatus.

SUMMARY OF THE INVENTION

From the foregoing, it is recognized that a need has arisen for commercially viable non-linear spectroscopy systems and methods. Further, a need has arisen for a non-linear spectroscopy system, providing simultaneous measurement of both amplitude and phase of second harmonic radiation over a broad spectral range without requiring superfluous system tuning or apparatus adjustment; and further providing parallel mode data acquisition, acquiring multiple wavelengths simultaneously, and increasing system speed and efficiency while overcoming the aforementioned limitations of conventional methods.

In the present invention, a frequency domain interferometric second harmonic (FDISH) spectroscopy system is provided for use in high volume commercial applications, such as semiconductor processing; providing non-linear (i.e. second harmonic) spectroscopy systems having unique diagnostic potential due (at least in part) to unusually high surface specificity and sensitivity; providing real time measurement during processing, parallel mode data acquisition, and a unique method of acquiring phase shift information in second harmonic radiation.

In one embodiment of the present invention, a method of spectroscopically analyzing amplitude and phase information of a particular sample comprises providing a femtosecond laser source positioned in an angularly distal relationship to the sample, generating from the laser source a primary light pulse of substantial peak intensity and spectral bandwidth directed at the sample, and providing a reference medium interposed between the light source and the sample, fixed in position with respect to the sample. A portion of the primary light pulse is directed through the reference medium generating a reference second harmonic signal directed at the sample, which propagates collinearly with the primary light pulse towards the sample. A spectrometer is provided, positioned in an angularly distal relationship to the sample and opposing the laser source, to receive second harmonic reflections of the primary pulse and reference signal from said sample. The second harmonic reflections received are then analyzed as desired by a user.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIGS. 1a and 1b are schematic representations of prior art spectroscopy systems;

FIGS. 3a, 3b, and 3c are representative plots comparing results of prior art systems with results of one embodiment of the present invention;

DETAILED DESCRIPTION OF THE INVENTION

Figure 2:
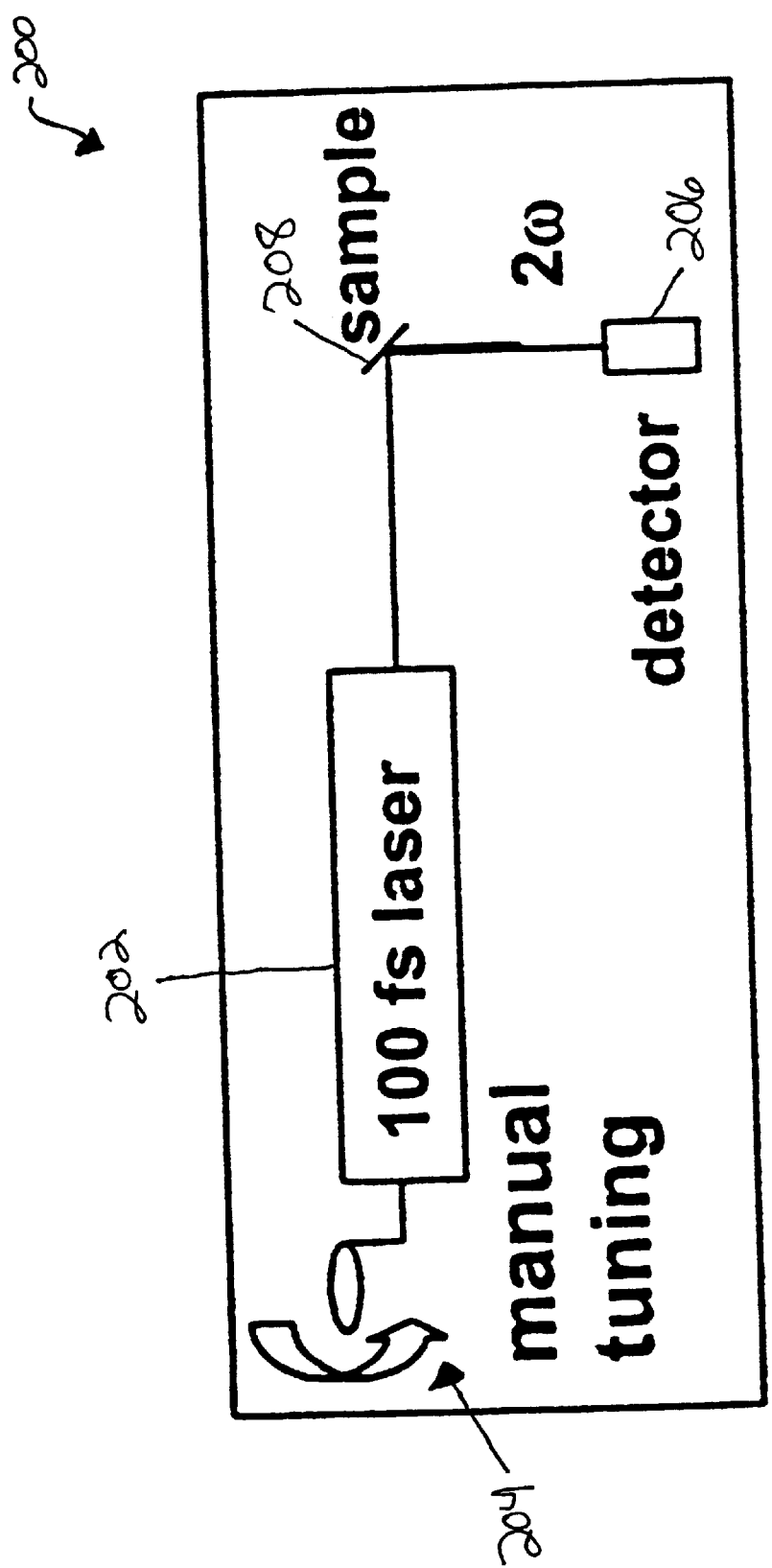
FIG. 2 is an illustrative block diagram of a prior art non-linear spectroscopy system.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

The present invention defines a frequency domain interferometric second harmonic (FDISH) spectroscopy system and method providing second harmonic (SH) spectroscopy viably for commercial applications. The present invention provides parallel mode data acquisition (i.e. acquiring multiple wavelengths simultaneously) and real time measurement during processing; as opposed to repetitively processing, then stopping to measure, then processing, etc. The present invention acquires phase shift information in parallel, providing increased system speed, accuracy, and efficiency over prior systems. The present invention further provides a unique method of acquiring phase shift information in SH radiation; obviating the need for superfluous apparatus adjustment and movement.

It should be understood that the principles and applications disclosed herein can be applied to spectroscopy systems in a number of applications. For purposes of explanation and illustration, the present invention is hereafter described in reference to non-linear spectroscopy employed in processing semiconductor devices.

Because of their high peak intensity, femtosecond laser pulses generate second harmonic (SH) radiation from weakly non-linear interfaces, such as Si(001) with great efficiency. The reflected SH radiation is sensitive to near-surface electric fields and surface conditions such as micro-roughness, strain, and adsorption. For determination of the resonant structure of the surface non-linear susceptibility, and for quantitative comparison with microscopic theories of SH generation, spectroscopic SH amplitude and phase measurements are essential.

The present invention applies to non-linear spectroscopy; previously employed in academic systems and methods, but heretofore commercially unviable. The present invention provides frequency domain non-linear interferometric spectroscopy performed without phase modulators, moving parts or separate optical paths for the interfering optical fields. This differs from time domain interferometric spectroscopy which requires phase modulation; often requiring moving parts which are difficult to control with necessary precision and thus represent a large source of noise in system measurement. Interferometry of fields produced by conventional optical interactions requires the separation of the optical beam into multiple parts, which must propagate through separate paths and interact with different optical components, and recombination of these separate beams with a tolerance much less than a wavelength; presenting a large source of noise in such measurements. The present invention involves no variable phase modulator, no moving parts, and fields produced therein propagate collinearly throughout the system obviating critical alignments.

As previously presented in reference to FIGS. 1a and 1b, the physical configuration of a conventional non-linear spectroscopy system is very similar to that of a conventional linear spectroscopy system. The light source in a non-linear system will usually be a laser instead of a lamp, because non-linear reflection is a weaker process than linear reflection and thus requires higher light intensity. Most other aspects (e.g. oblique incidence, spectrometer, optical elements, detector) will be quite similar. One exception is that the spectrometer in a non-linear spectroscopy system is adjusted to collect a different color range. In the case of SH spectra, the spectrometer is adjusted to examine double the frequency of the incident light; and the detector is correspondingly adjusted to be sensitive to those colors.

In conventional non-linear spectroscopy systems, this adjustment is a repetitive process. In the present invention, the spectrometer and/or detector is adjusted to the frequencies of concern only once. Once set, further adjustment is unnecessary.

Figure 3A:
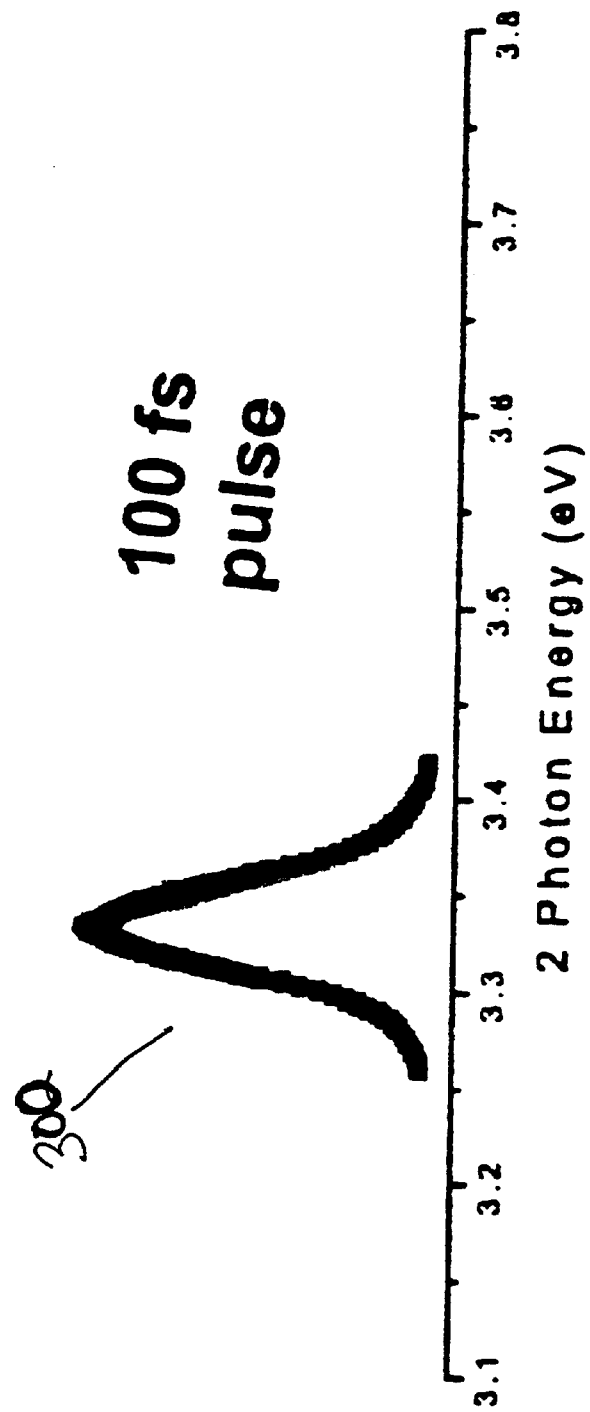
Figure 3C:
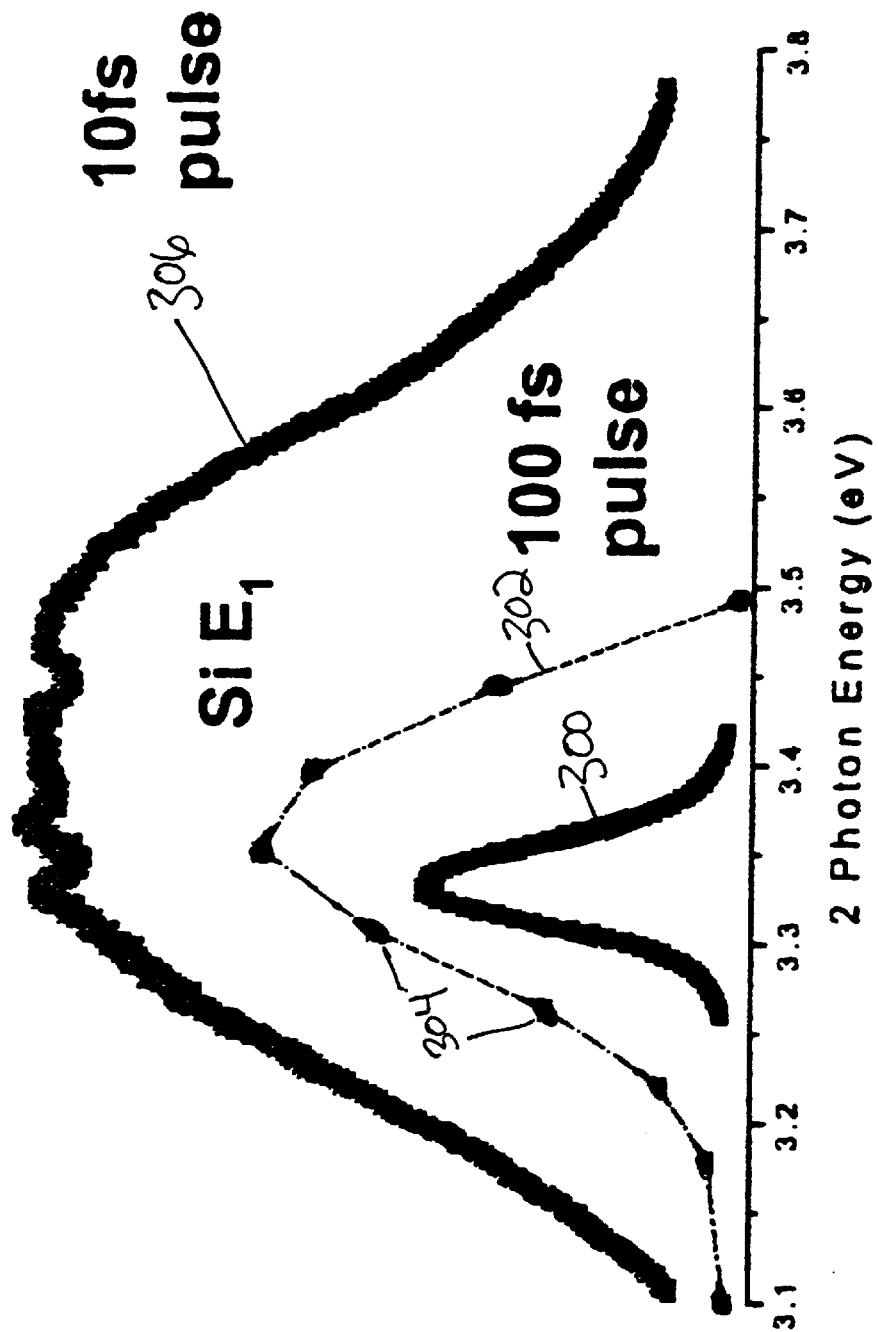
Figure 4:
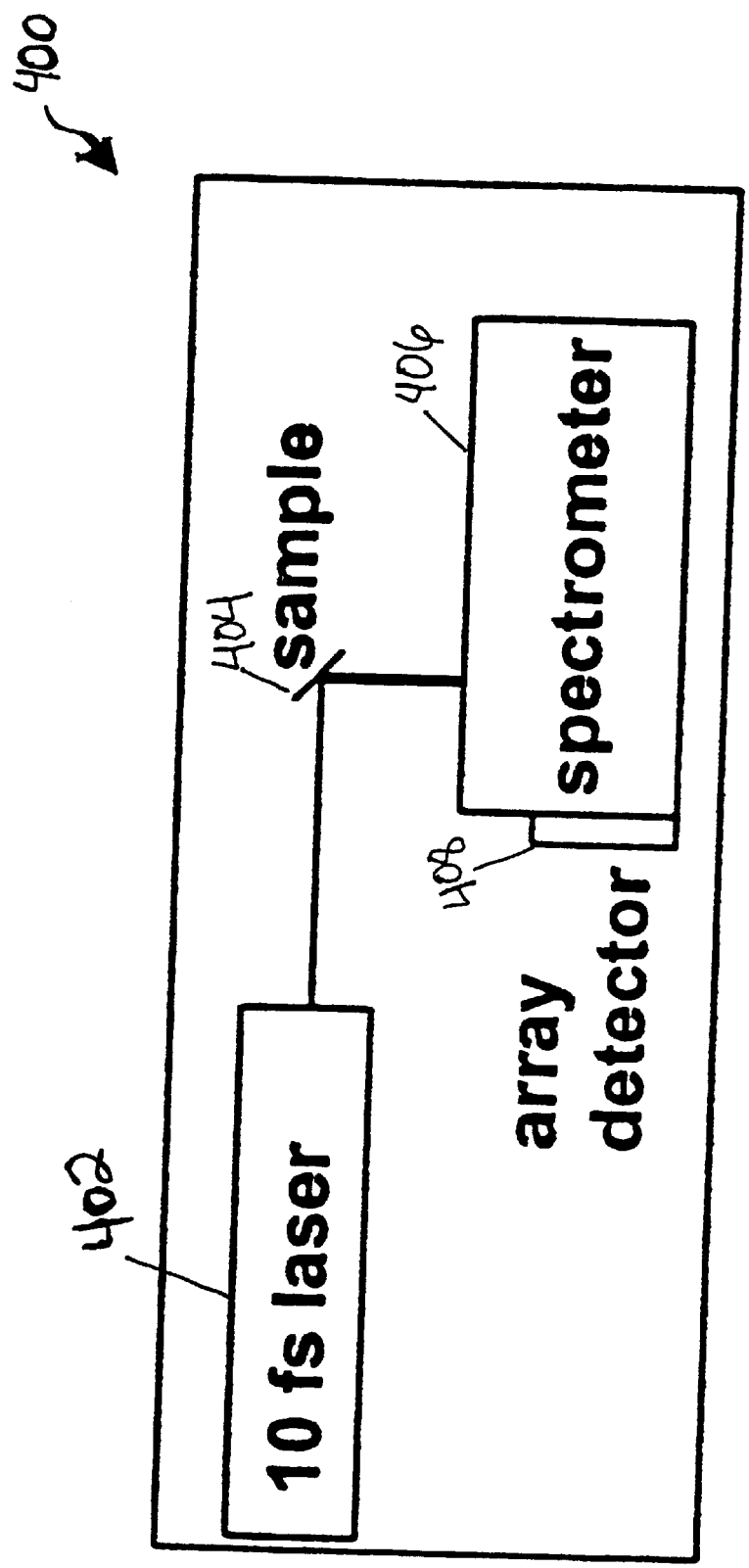
FIG. 4 is an illustrative block diagram of an embodiment of the present invention.

This difference is now further illustrated with reference to FIGS. 2, 3a–3c, and 4. Referring now to FIG. 2, a simple diagram of a conventional SH spectroscopy system 200 is shown. Conventional measurements of SH spectra in such systems have been made using a laser source 202 with pulses of 100 femtosecond (fs) duration. Such pulses have narrow spectral bandwidths, as illustrated by curve 300 in FIG. 3a. In order to adequately measure the spectral response of a given sample, adjustments must be made to tune the laser in system 200. Laser 202 is typically manually adjusted 204 to tune the optical frequency of the pulses across a broad spectral range; and the SH is detected by a single element detector 206 at each point to measure the cumulative spectral response of a sample 208. Measurement by such methods typically requires several minutes to execute. The resultant spectrum 302 is shown in FIG. 3b. Plot points 304 represent the measurement taken for each manual adjustment of laser 202. In contrast, a spectroscopy system 400 in accordance with the present invention, as shown in FIG. 4, utilizes a laser 402 with a pulse duration in the range of 10–15 fs. Such lasers provide a very large spectral bandwidth 306 as shown in FIG. 3c.

The present invention exploits the broad bandwidth and coherence of such pulses; providing a robust and highly efficient method for measuring the spectral amplitude and phase of reflected SH radiation without laser tuning. The spectra of such pulses are broader than solid state critical-point features of a sample (such as sample 404 from FIG. 4); thus allowing parallel acquisition of SH spectra by dispersion of the reflected SH radiation in a spectrometer 406 equipped with an array detector 408. Measurements with a system such as system 400 can be made in a few seconds.

The present invention provides amplitude and phase measurement of SH generated by a particular sample; allowing for a full spectrum characterization in the frequency domain. In contrast, conventional methods generally provide only a partial characterization; only measuring the amplitude of SH generated by a sample.

Attempts have been made to use conventional non-linear SH spectroscopy systems to provide phase measurement as well. For example, this has been done in the past with 100 fs laser pulses, by measuring time domain interferograms. In such methods, a 100 fs laser pulse is polarization filtered, then focused onto a sample through a reference material which is mounted on a translating stage. A SH reference pulse ($2\omega_{ref}$) is generated in the reference material; which then propagates along with the original laser pulse, delayed in time behind the original laser pulse by the dispersion of air. The original laser pulse reflects from the sample and generates a sample SH pulse ($2\omega_{sample}$). The reference pulse also reflects from the sample; and both SH pulses ($2\omega_{sample}$ and $2\omega_{ref}$) then propagate into a detector, separated in time by a delay determined by the distance between the translatable reference and the sample. As this time delay is varied by adjusting the translatable reference, the interference of the two SH pulses causes oscillations in the signal received at the detector; which may then be analyzed to determine SH phase. This time consuming measurement is repeated for each laser frequency to obtain a desired phase spectrum, one wavelength at a time; resulting in a serial mode of data acquisition.

Figure 5:
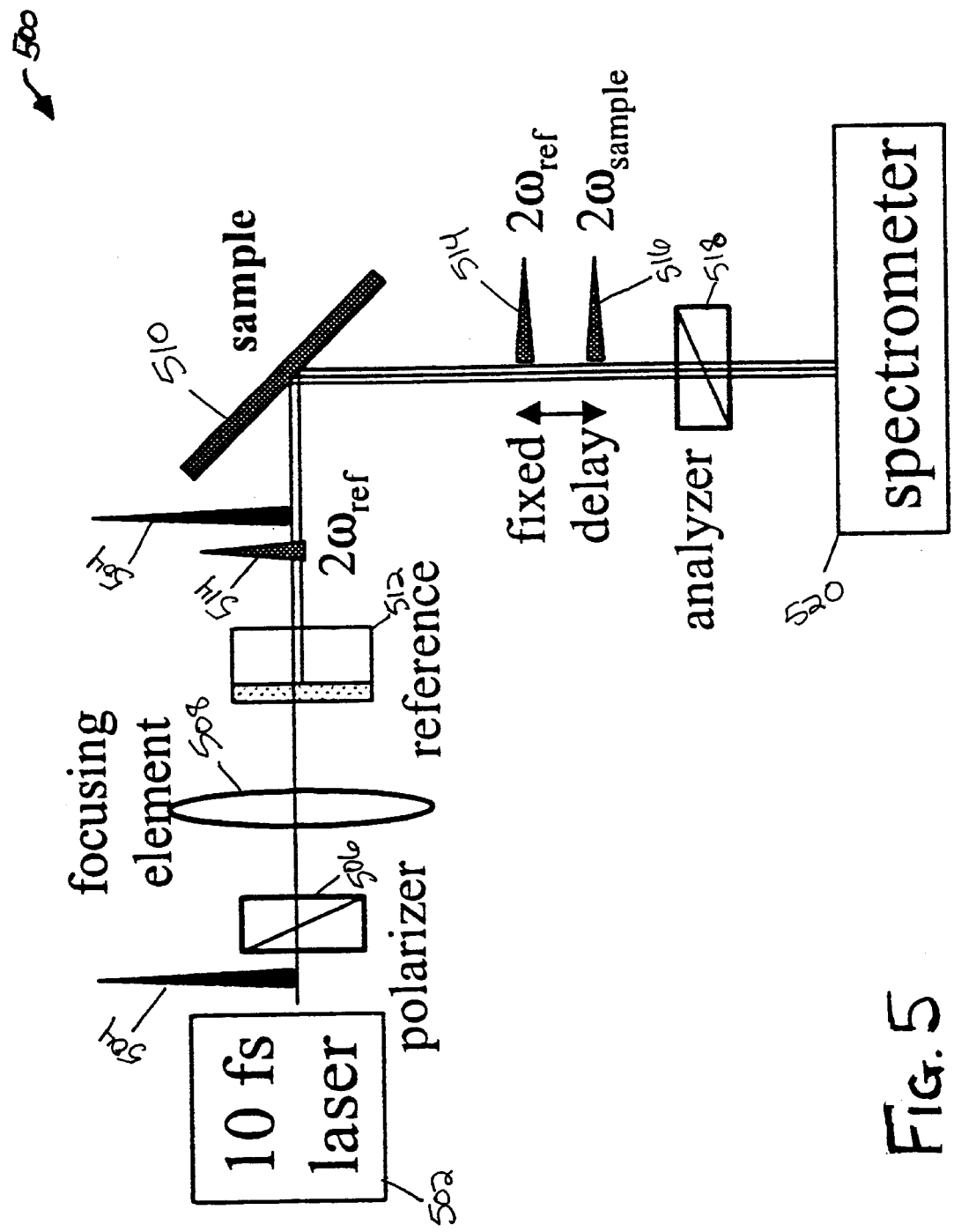
FIG. 5 is a schematic representation of an embodiment of the present invention.

The present invention eliminates the necessity of varying the time delay, and provides for parallel mode data acquisition by shifting interferometric analysis to the frequency domain. Referring now to FIG. 5, a diagram of a spectroscopy system 500 further illustrating advantages of the present invention is depicted. System 500 represents one possible embodiment of a non-linear, SH spectroscopy system according to the present invention. System 500 comprises a light source 502. In this embodiment, source 502 comprises a 10 fs laser. The present invention may be practiced with lasers having pulse duration of ~10–15 fs; although pulses of duration <10 fs permit more effective practice of the teachings herein. Other light sources, having sufficient spectral bandwidth for measuring SH phase for the full spectrum in parallel, may also be used in accordance with the present invention.

Source 502 emits source laser pulse 504. Pulse 504 is filtered through polarizing element 506, and focused by focusing element 508 onto a sample 510 through a reference medium 512. Reference medium 512 is fixed, and does not require adjustment or tuning. As pulse 504 channels through reference 512, a SH reference pulse 514 ($2\omega_{ref}$) is generated. Pulses 504 and 514 propagate collinearly towards sample 510.

Source pulse 504 reflects from sample 510, generating a SH sample pulse 516 ($2\omega_{sample}$). Reference pulse 514 also reflects from sample 510; trailing pulse 516 by a fixed time delay which corresponds to the distance between reference 512 and sample 510. Pulses 514 and 516 propagate through analyzer 518 and are detected and/or analyzed by spectrometer 520. Based on pulses 514 and 516, spectrometer 520 renders both amplitude and phase shift information for analysis of sample 510.

The present invention does not require apparatus movement as in conventional systems. The present invention provides a unique parallel method of acquiring phase shift information in SH radiation; providing increased system speed, accuracy, and efficiency over prior systems.

Figure 6:
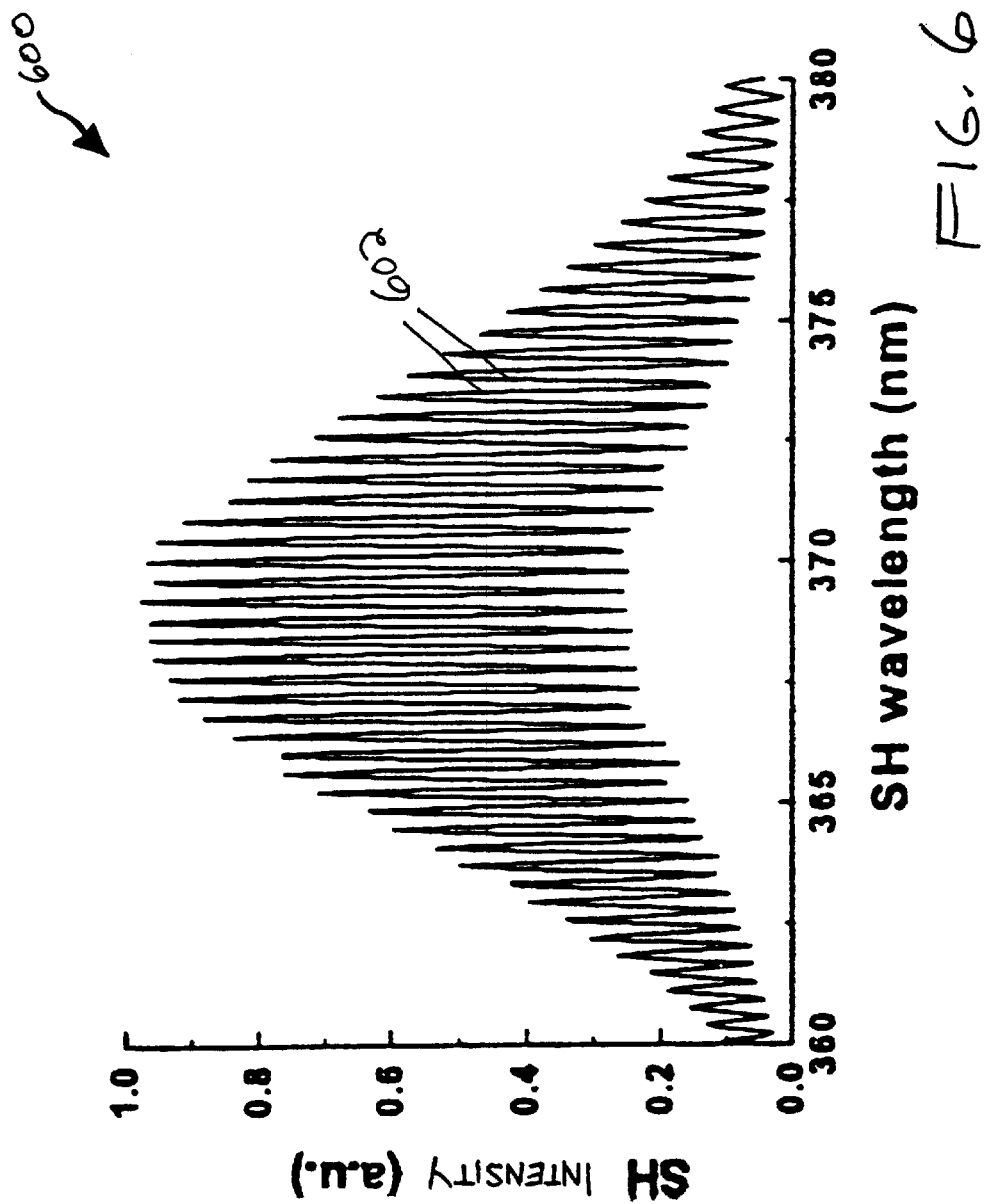
FIG. 6 is a representative plot of results obtained with the embodiment of FIG. 5.

FIG. 6 shows the spectra 600 resulting from the process described in relation to FIG. 5. Spectra 600 is characterized by oscillations 602; which are analyzed with spectral interferometry techniques to yield full-range SH spectra in a single measurement. The spectra spans a broad range of wavelengths, which may then be processed or analyzed in parallel by a spectrometer and/or array detector.

Thus the present invention utilizes a femtosecond laser to source light pulses of short duration (~15 fs or less) having a wide wavelength content. The light pulses are directed at and reflect off a desired sample or workpiece; and propagate into a spectrometer/array detector system. Prior to interaction with the sample or workpiece, a sourced light pulse channels through a beam splitting member. This beam splitting member directs a portion of the source light towards the sample; and directs another portion through a reference medium, fixed in positional relationship to the sample or workpiece. For example, $SnO_2$ on a glass substrate may be used to provide the beam splitting and reference medium functions. The sourced light pulse propagates to, and reflects from, the sample. This pulse has sufficient intensity to generate a sample second harmonic signal, carrying phase and spectral characteristics for analysis at the spectrometer/array detector system. The light pulse directed through the reference medium generates a reference second harmonic signal. The reference second harmonic pulse is of a relatively weak intensity; and therefore remains substantially unaltered as it reflects from the surface of the sample.

The spectral phase of the sample's second harmonic signal may be determined by propagation of the reference and sample SH pulses collinearly and sequentially into the spectrometer, where they create frequency domain interferograms. Fourier analysis of these interferograms yields the spectral phase. The present invention thus provides frequency domain interferometric second harmonic (FDISH) spectroscopy.

As such, interferometric analysis of the source light second harmonic spectra and the reflected reference second harmonic spectra provides for second harmonic phase measurement and sample characterization. The reference medium has a known composition and known second harmonic properties and behaviors. The reference second harmonic is independent of the sample properties. The fixed relationship of the reference medium and its known properties therefore provide a basis for interferometric analysis (i.e. comparison) of the source light second harmonic spectra; characterizing the sample or workpiece under analysis. This process may operate continuously, providing for real-time identification and analysis of changes in material properties of the sample. Those skilled in the art should appreciate that the reflected second harmonic spectra characterize the surface and interface regions of the sample or workpiece under analysis. Changes in the material properties, e.g. changes in chemical reactivity, is an example of properties that acquired second harmonic spectrum would be sensitive to. Second harmonic phase information also provides valuable characterization of the sample or workpiece under analysis. The present invention acquires second harmonic spectrum and phase information quickly and in real time.

The present invention thus provides for real time measurement during processing; as opposed to processing, then stopping to measure, then processing, etc. The present invention provides parallel mode data acquisition; acquiring multiple wavelengths simultaneously, and providing second harmonic phase data, increasing overall system speed and efficiency.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A non-linear spectroscopy system for analyzing a particular sample, said system comprising:
   a light source, positioned in an angularly distal relationship to said sample, for generating a primary pulse of substantial peak intensity and spectral bandwidth directed at said sample;
   a reference medium interposed between said light source and said sample, in a fixed position with respect to said sample, for generating a reference signal also directed at said sample; and
   a spectrometer, positioned in an angularly distal relationship to said sample for receiving reflections of the primary pulse and reference signal from said sample.

2. The system of claim 1 wherein said light source is a femtosecond laser.

3. The system of claim 2 wherein said femtosecond laser sources light with a pulse duration of less than 15 femtoseconds.

4. The system of claim 2 wherein said femtosecond laser sources light with a pulse duration of approximately 10 femtoseconds.

5. The system of claim 1 wherein reference medium generates a second harmonic reference signal.

6. The system of claim 5 wherein at least a portion of the primary pulse is directed through the reference medium to generate the second harmonic reference signal.

7. The system of claim 1 wherein said spectrometer is further positioned, with respect to said sample, in an opposing relationship to the light source.

8. The system of claim 1 further comprising an array detector coupled to the spectrometer for detecting spectra of the reflections received by the spectrometer.

9. The system of claim 1 further comprising a polarizing optical element interposed between the light source and the reference medium.

10. A method of spectroscopically analyzing amplitude and phase of second harmonic radiation characterizing a particular sample, said method comprising the steps of:
    providing a light source positioned in an angularly distal relationship to said sample;
    generating from the light source a primary light pulse of substantial peak intensity and spectral bandwidth directed at said sample;
    providing a reference medium interposed between the light source and said sample, in a fixed position with respect to said sample;
    generating from the reference medium a reference signal directed at said sample;
    providing a spectrometer, positioned in an angularly distal relationship to said sample to receive second harmonic reflections of the primary pulse and reference signal from said sample; and
    receiving and analyzing the second harmonic reflections.

11. The method of claim 10 wherein the step of providing a light source further comprises providing a femtosecond laser.

12. The method of claim 11 wherein the step of generating a primary light pulse further comprises generating a light pulse with a duration of less than 15 femtoseconds.

13. The method of claim 11 wherein the step of generating a primary light pulse further comprises generating a light pulse with a duration of approximately 10 femtoseconds.

14. The method of claim 11 wherein the step of generating a reference signal further comprises generating a second harmonic reference signal.

15. The method of claim 14 wherein the step of generating a second harmonic reference signal further comprises directing at least a portion of the primary light pulse through the reference medium to generate the second harmonic reference signal.

16. The method of claim 14 wherein the step of generating a second harmonic reference signal further comprises directing the second harmonic reference signal at said sample collinearly with, and in a known delay from, the primary light pulse.

17. The method of claim 14 wherein the step of providing a spectrometer further comprises positioning the spectrometer in an opposing relationship, with respect to said sample, to the light source.

18. The method of claim 17 wherein the step of providing a spectrometer further comprises providing an array detector coupled to the spectrometer.

19. The method of claim 18 wherein the step of receiving and analyzing the second harmonic reflections further comprises utilizing the array detector to detect spectra of the second harmonic reflections received.

20. A system for analyzing a particular sample using frequency domain interferometric second harmonic spectroscopy, said system comprising:

a femtosecond laser source, positioned in an angularly distal relationship to said sample, for generating a primary pulse having a pulse duration of approximately ten femtoseconds, wherein the primary pulse is directed at said sample;

a reference medium interposed between said femtosecond laser source and said sample in a fixed position with respect to said sample, wherein the primary pulse propagates through the reference medium generating a reference signal also directed at said sample; and a spectrometer system, positioned in an angularly distal relationship to said sample and in an opposing relationship to said femtosecond laser source with respect to said sample, for receiving spectra resulting from reflection of the primary pulse and reference signal from said sample.

* * * * *